(12) United States Patent
Harder et al.

(10) Patent No.: US 7,652,071 B2
(45) Date of Patent: Jan. 26, 2010

(54) PENETRATION OF ACTIVE SUBSTANCES INTO CELLS AND ORGANS

(75) Inventors: Achim Harder, Köln (DE); Iris Heep, Köln (DE); Stefan Herrmann, Langenfeld (DE); Jeffry-Lynn Grunkemeyer, Pratteln (CH); Jochen Kalbe, Leichlingen (DE); Heinz Mehlhorn, Neuss (DE); Jürgen Schmidt, Düsseldorf (DE); Günther Schmahl, Köln (DE)

(73) Assignees: Alpha-Biocare GmbH, Dusseldorf (DE); Convet GmbH & Co. KG, Dusseldorf (DE)

(*) Notice: Subject to any disclaimer, the term of this patent is extended or adjusted under 35 U.S.C. 154(b) by 216 days.

(21) Appl. No.: 10/551,882

(22) PCT Filed: Mar. 25, 2004

(86) PCT No.: PCT/EP2004/003155

§ 371 (c)(1),
(2), (4) Date: Jan. 15, 2007

(87) PCT Pub. No.: WO2004/087117

PCT Pub. Date: Oct. 14, 2004

(65) Prior Publication Data

US 2007/0270503 A1    Nov. 22, 2007

(30) Foreign Application Priority Data

Apr. 2, 2003    (DE) ................... 103 14 976

(51) Int. Cl.
*A61K 47/00*    (2006.01)
*A61K 31/665*    (2006.01)

(52) U.S. Cl. .......... 514/772; 514/101; 514/946; 514/777; 424/9.2; 424/449; 435/40.5; 436/149

(58) Field of Classification Search ........... 514/101, 514/946, 772, 777, 788, 789; 424/9.2, 449; 435/40.5
See application file for complete search history.

(56) References Cited

U.S. PATENT DOCUMENTS

| 3,004,894 | A |   | 10/1961 | Johnson et al. |            |
|-----------|---|---|---------|----------------|------------|
| 4,557,934 | A | * | 12/1985 | Cooper         | 514/159    |
| 4,861,764 | A | * | 8/1989  | Samour et al.  | 514/177    |
| 5,837,289 | A | * | 11/1998 | Grasela et al. | 424/484    |

FOREIGN PATENT DOCUMENTS

| EP | 0 268 460 B1   | 5/1988 |
| EP | 0 552 879 B1   | 7/1993 |
| EP | 0 728 462 B1   | 8/1996 |
| WO | WO 99/09954 A1 | 3/1999 |
| WO | WO 99/20257 A1 | 4/1999 |
| WO | WO 03/028702 A1| 4/2003 |

OTHER PUBLICATIONS

Piasecki et al, abstract for PL 175837, Preparation of long-chain cis-nand trans-2-alkyl-5-hydroxy-1, 3 -dioxanes, 1994.*
Fuhrman Jr., L. C., et al., "Effect of Novel Penetration Enhancers on the Transdermal Delivery of Hydrocortisone: An in Vitro Species Comparison", J. Controlled Release, 45: 199-206 (1997).
Hui, X., et al., "Enhanced Econazole Penetration Into Human Nail by 2-n-nonyl-1,3-dioxolane", J. Pharm. Sciences, 92(1): 142-148 (Oct. 2002).

* cited by examiner

*Primary Examiner*—Ardin Marschel
*Assistant Examiner*—Savitha Rao
(74) *Attorney, Agent, or Firm*—Rankin, Hill & Clark LLP

(57) ABSTRACT

The invention relates to the use of certain cyclic acetals or ketals for improving the penetration of pharmaceutical agents into cells and organs.

11 Claims, No Drawings

PENETRATION OF ACTIVE SUBSTANCES INTO CELLS AND ORGANS

The present invention relates to the use of certain cyclic acetals or ketals for improving the penetration of pharmaceutically active substances into cells and organs.

Larval stages of helminths, adult helminths, protozoans, a series of microorganisms (bacteria, fungi, viruses and the like) and tumors attack internal organs of humans and animals, for example brain, liver, muscles and the like. In such a case, the current anthelminthics, antiprotozoals, antibiotics, virostats, chemotherapeuticals, vaccines and modulators of the specific and unspecific immune response and the like are frequently effective only at high dosage rates, or not at all. The difficulty is that cell or organ barriers, such as, for example, cell membranes, the blood-brain barrier and the placental barrier, are not readily permeated by a wide range of chemotherapeuticals.

The use of dialkyldioxolanes as surface-active substances (surfactants) has already been disclosed (see, for example, WO 00/70334 or U.S. Pat. No. 3,948,953).

WO 01/17345 describes the use of certain acetals or ketals for the preparation of biodegradable solutions of bioactive compounds, viz. herbicides, safeners, insecticides, fungicides, acaricides, nematicides, pheromones and repellents.

WO 99/09954 describes the use of 2-nonyl-1,3-dioxolane and other hydrocarbyl derivatives of 1,3-dioxolane or 1,3-dioxane for improving the skin penetration when pharmaceuticals are applied dermally. Active substances which are mentioned are ibuprofen and other NSAIDs.

In Drug Delivery (2), (1995), 117-22, Michniak et al. describe in-vitro studies on the skin of nude mice with the aim of establishing structure-activity relationships for 2-(1-nonyl)-1,3-dioxolane derivatives for improving the skin penetration of hydrocortisone (by way of model).

In J. Pharm. Soci. 84 (12) (1995), 1427-33, Phillips et al. describe studies into the transdermal administration of pharmaceuticals with different lipophilicity using ozone analogs as skin penetration enhancers. One of the compounds tested was 2-(1-nonyl)-1,3-dioxolane.

Erdlenbruch et al. (Exp. Brain Res. 135 (2000) 417-422) studied the transient and controllable opening of the blood-brain barrier for cytostatic and antibiotic agents in rats. However, they used alkylglycerols, which they applied intraarterially into the carotid artery.

There remains a need for penetration enhancers which improve the permeability of cell and organ barriers for pharmaceuticals so that the latter can reach the site of the pathological process. The pharmaceuticals would thereby be able to act either more rapidly or at lower dosages than conventionally employed, and compounds which were hitherto inactive might become active only as a result of the addition of such penetration-enhancing compounds.

Surprisingly, it has now been found that this object can be achieved with the aid of certain cyclic acetals. The invention therefore relates to the use of compounds of the formula (I),

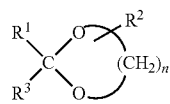

(I)

in which $R^1$ represents an alkyl, alkenyl or alkynyl radical which has 2 to 30 carbon atoms and which is optionally substituted by one or more halogen atoms, where, if appropriate, one or more suitable nonadjacent carbon chain members can be replaced by oxygen atoms, $R^2$ represents hydrogen, hydroxyl, —$NH_2$, —$NR^4R^5$, —$N^+(R^4R^5R^6)$, —$PR^7R^8$, —O—$P(R^7R^8)$, —$P(O)R^7R^8$, —$P^+(R^7R^8R^9)$ or a $C_{1-5}$-alkyl radical which is optionally substituted by hydroxyl, $C_{1-4}$-alkoxy, —$NH_2$, mono- or di-$C_{1-4}$-alkylamino or a 5- to 7-membered heterocycle having up to three hetero atoms selected from among O, N and S, $R^3$ represents hydrogen or can have the meanings stated above for $R^1$, $R^4$, $R^5$ and $R^6$ independently of one another represent hydrogen or $C_{1-5}$-alkyl or two of the radicals together with the nitrogen atom to which they are bonded form a 5- to 7-membered heterocycle which can optionally additionally comprise one or two further heteroatoms selected from among O, N and S, $R^7$, $R^8$ and $R^9$ independently of one another represent $C_{1-5}$-alkyl, $C_{1-5}$-alkoxy or $C_{6-12}$-aryl or two of the radicals together with the phosphorus atom to which they are bonded form a 5-7-membered heterocycle which can optionally additionally comprise one or two further heteroatoms selected from among O, N and S, n denotes 2, 3 or 4, for the preparation of pharmaceuticals with improved permeation of a pharmaceutically active substance across cell and organ barriers.

Alkyl radicals can generally be straight-chain or branched. This also applies to alkyl radicals in other substituents, such as, for example, alkoxy or alkylamino.

Alkenyl and alkynyl radicals can likewise be straight-chain or branched and comprise one or more double or triple bonds, depending on the number of carbons; alkenyl and alkynyl radicals preferably comprise one double or triple bond.

$C_{6-12}$-Aryl represents a carbocyclic aromatic radical having 6 to 12 carbon atoms, for example phenyl or naphthyl.

Heterocycle can represent for example pyrrolidine, piperidine, piperazine, hexamethyleneimine, hexahydro-1,3,5-triazine, morpholine.

$R^1$ preferably represents an n-alkyl radical which has 2 to 20 carbon atoms and which is optionally substituted by one or more fluorine or chlorine atoms, in which n-alkyl radical one of the carbon chain members can be replaced by an oxygen atom.

$R^1$ especially preferably represents an n-alkyl radical having 5 to 12 carbon atoms.

If $R^1$ represents an alkyl radical which can be interrupted by one or more oxygen atoms, the acetal ring is preferably attached via a carbon atom of the radical $R^1$.

$R^2$ preferably represents hydroxyl, $C_{1-3}$-alkyl which is optionally substituted by hydroxyl or $C_{1-5}$-alkoxy.

$R^2$ especially preferably represents OH or —$CH_2OH$.

$R^3$ preferably represents hydrogen.

n preferably represents the numbers 2 or 3.

If appropriate, the compounds of the formula (I) can exist as geometric and/or optical isomers or their variously composed isomer mixtures, depending on the type and number of substituents. Both the pure isomers and the isomer mixtures can be used in accordance with the invention.

Mixtures of different compounds of the formula (I) can furthermore also be used in accordance with the invention.

The compounds of the formula (I) which are used in accordance with the invention can also be employed in the form of pharmaceutically acceptable salts, provided they have suitable substituents attached to them. Pharmaceutically acceptable salts can be salts with inorganic or organic acids, such as, for example, hydrochloric acid, acetic acid, maleic acid. Pharmaceutically acceptable salts can also be salts with bases, such as, for example, metal or ammonium salts, for example alkali metal salts, such as sodium or potassium salts, or ammonium salts, for example with triethylamine, triethanolamine or arginine.

The compounds of the formula (I) and their preparation are known to the skilled worker; if appropriate, they may be prepared analogously to known processes. Reference is made for example to WO 01/17345 or Tenside Detergents 1980, 17, 21-24.

Examples of compounds which can especially preferably be used are the following compounds of the formulae (A) and (B)

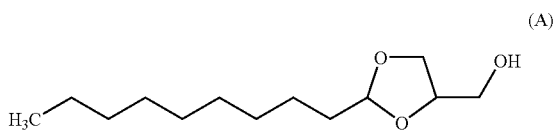
(A)

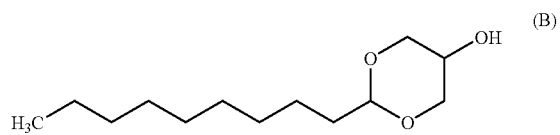
(B)

The compounds of the formula (I) which are used in accordance with the invention are suitable in principle for improving the penetration of cell and organ barriers for the widest range of pharmaceuticals where this is required or makes sense. Examples which may be mentioned are anthelminthics, antiprotozoals, antibiotics, virostats, chemotherapeuticals, vaccines, modulators of the specific and unspecific immune response, and pharmaceuticals for the treatment of CNS diseases. The following list provides examples of diseases in humans and animals together with examples of active substances for their treatment where the use according to the invention of compounds of the formula (I) is advantageous:

| 1. Parasites (humans) | | |
|---|---|---|
| a) | Toxoplasma, e.g. *T. gondii* (brain) | pyrimethamine/sulfadiazine |
| b) | Chagas' disease (heart, nerves) | nifurtimox/benznidazole |
| c) | *Pneumocystis carinii* (lungs) | cotrimoxazole/trimethoprim |
| d) | *Filaria* species (tissue) | diethylcarbamazine, macrocyclic lactones (avermectins, milbemycins) |
| e) | *Trichina* species (muscles) | mebendazole, thiabendazole |
| f) | pathogens causing sleeping sickness (brain) | suramin, melarsoprol, eflornithin |
| g) | pathogens causing leishmaniosis (skin, inner organs) | pentavalent antimony products, pentamidines, meglumine antimoniate |
| h) | Angiostrongylus | mebendazole and thiabendazole, macrocyclic lactones (e.g. avermectins, milbemycins), depsipeptides (e.g. emodepsid, PF 1022A) |
| i) | *Toxocara* larva migrans in the body | mebendazole and thiabendazole |
| j) | *Echinococcus* cysts (liver) | mebendazole and albendazole halts growth |
| k) | amoebic abscess in the liver | nitroimidazoles, dehydroemetine, paromomycin |
| l) | *microsporidia* | albendazole |
| m) | trematodes | praziquantel |
| n) | tapeworm *cysticerci* | praziquantel |
| 2. Parasites (animals) | | |
| a) | *Toxocara* larvae in the dam | benzimidazoles (bendazoles) |
| b) | *coccidia* (chickens/cattle; intestines) | toltrazuril, ponazuril, ionophorene |
| c) | nematodes (intestines) | broad range of anthelminthics and their combinations (e.g. febantel, pyrantel) |
| d) | *Fasciola hepatica* | salicylanilides, triclabendazole, Clorsulon, diamfenetid, praziquantel |
| e) | *Trichina* (muscular system) | mebendazole and thiabendazole |
| f) | *Cryptosporidium* species | halofuginone |
| g) | hammondia/Neospora/Toxoplasma | toltrazuril |
| h) | *Cysticerci, spargana* of tapeworm species | praziquantel |
| i) | adult tapeworms (intestines) | niclosamide/praziquantel |
| j) | pathogens causing leishmaniosis (dogs) | pentamidines, antimony compounds |
| k) | heartworm/*Dirofilaria* (dogs) | macrocyclic lactones (avermectins, milbemycins), depsipeptides (emodepsid, PF 1022 A) |
| i) | pathogens causing mange, demodecosis (dogs, cats, pigs) | macrocyclic lactones (avermectins, milbemycins) |

-continued

| | 3. Bacteria (humans/animals) | |
|---|---|---|
| a) | brain (e.g. *meningococci*) | antibiotics |
| b) | lungs (e.g. *pneumococci*) | antibiotics |
| c) | heart/intestines (e.g. *helicobacter*, *Chlamydia* species) | antibiotics |
| d) | nerves (e.g. *Borrelia burgdorferi*) | antibiotics |
| | 4. Carcinomas (humans/animals) | |
| a) | brain, lungs, liver, bones and the like | cytostats |
| | 5. Diseases of the CNS | |
| a) | mental disorders | e.g. antidepressants |
| b) | Alzheimer's disease | |
| c) | Parkinson's disease | |
| d) | schizophrenia | |

Stroke

Improving the penetration of cell and organ barriers means in particular an improved penetration across the blood-brain barrier, the placental barrier and improved penetration into cells of the muscles and liver. Using the compounds according to the invention, it is now possible for the first time to achieve effective active substance concentrations in organs in which this would otherwise be almost impossible, for example also in the case of the oral administration of conventional active substance doses. An important example which may be mentioned is the very poor permeability of the blood-brain barrier for many of the abovementioned active substances.

Active substances whose transport across cell and organ barriers can be improved by means of the compounds of the formula (I) according to the invention and which may be mentioned are in particular those which follow:

Antibiotics which may be mentioned by way of example are the fluoroquinolones. Fluoroquinolones are, inter alia, compounds as are disclosed in the following documents: U.S. Pat. No. 4,670,444 (Bayer AG), U.S. Pat. No. 4,472,405 (Riker Labs), U.S. Pat. No. 4,730,000 (Abbott), U.S. Pat. No. 4,861,779 (Pfizer), U.S. Pat. No. 4,382,892 (Daiichi), U.S. Pat. No. 4,704,459 (Toyama), with the following being mentioned as specific examples: benofloxacin, binfloxacin, cinoxacin, ciprofloxacin, danofloxacin, difloxacin, enoxacin, enrofloxacin, fleroxacin, ibafloxacin, levofloxacin, lomefloxacin, marbofloxacin, moxifloxacin, norfloxacin, ofloxacin, orbifloxacin, pefloxacin, pipemidic acid, temafloxacin, tosufloxacin, sarafloxacin, sparfloxacin.

A preferred group of fluoroquinolones are those of the formula (II) or (III):

(II)

(III)

in which

X represents hydrogen, halogen, $C_{1-4}$-alkyl, $C_{1-4}$-alkoxy, $NH_2$,

Y represents radicals of the structures where
$R^4$ represents optionally hydroxyl- or methoxy-substituted straight-chain or branched $C_1$-$C_4$-alkyl, cyclopropyl, acyl having 1 to 3 C atoms,
$R^5$ represents hydrogen, methyl, phenyl, thienyl or pyridyl,
$R^6$ represents hydrogen or $C_{1-4}$-alkyl,
$R^7$ represents hydrogen or $C_{1-4}$-alkyl,
$R^8$ represents hydrogen or $C_{1-4}$-alkyl, and
$R^1$ represents an alkyl radical having 1 to 3 carbon atoms, cyclopropyl, 2-fluoroethyl, methoxy, 4-fluorophenyl, 2,4-difluorophenyl or methylamino,
$R^2$ represents hydrogen or optionally methoxy- or 2-methoxyethoxy-substituted alkyl having 1 to 6 carbon atoms, and cyclohexyl, benzyl, 2-oxopropyl, phenacyl, ethoxycarbonylmethyl, pivaloyloxymethyl, R³ represents hydrogen, methyl or ethyl and A represents nitrogen, =CH—, =C(halogen)-, =C(OCH₃)—, =C(CH₃)— or =C(CN), B represents oxygen, optionally methyl- or phenyl-substituted =NH or =CH₂, Z represents =CH— or =N—, and their pharmaceutically useful salts and hydrates.

The compounds of the formulae (II) and (III) can exist in the form of their racemates or in enantiomeric forms.

Preferred compounds of the formula (II) are those in which

A represents =CH— or =C—CN,

R¹ represents optionally halogen-substituted $C_1$-$C_3$-alkyl or cyclopropyl,

R² represents hydrogen or $C_{1-4}$-alkyl,

Y represents radicals of the structures

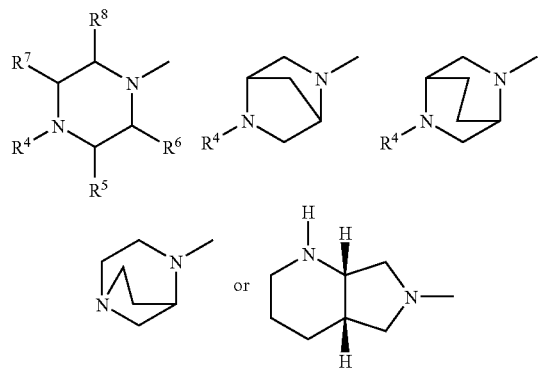

where

R⁴ represents optionally hydroxyl-substituted straight-chain or branched $C_1$-$C_3$-alkyl, oxalkyl having 1 to 4 C atoms, R⁵ represents hydrogen, methyl or phenyl, R⁷ represents hydrogen or methyl, and their pharmaceutically useful hydrates and salts.

Especially preferred compounds of the formula (II) are those in which

A represents =CH— or =C—CN,

R¹ represents cyclopropyl,

R² represents hydrogen, methyl or ethyl,

Y represents radicals of the structures

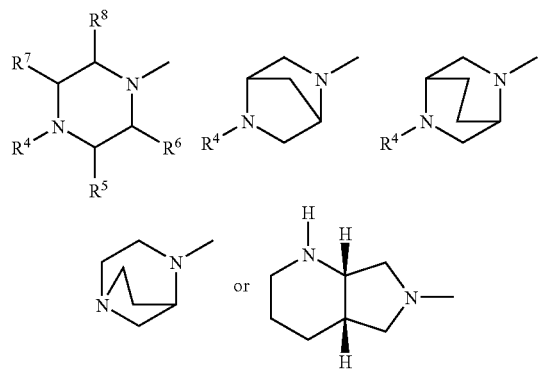

where

R⁴ represents methyl, optionally hydroxyl-substituted ethyl,

R⁵ represents hydrogen or methyl,

R⁷ represents hydrogen or methyl, and their pharmaceutically useful salts and hydrates.

Suitable salts are basic salts and acid addition salts which are pharmaceutically useful.

Salts which are understood as being pharmaceutically useful are, for example, the salts of hydrochloric acid, sulfuric acid, acetic acid, glycolic acid, lactic acid, succinic acid, citric acid, tartaric acid, methanesulfonic acid, 4-toluenesulfonic acid, galacturonic acid, gluconic acid, embonic acid, glutamic acid or aspartic acid. Furthermore, the compounds according to the invention can be bound to the acidic or basic ion exchangers. Basic salts which may be mentioned as being pharmaceutically useful are the alkali metal salts, for example the sodium or potassium salts, the alkaline earth metal salts, for example the magnesium or calcium salts; the zinc salts, the silver salts and the guanidinium salts.

Hydrates are understood as meaning the hydrates of the fluoroquinolones themselves and the hydrates of their salts.

Fluoroquinolones which may be mentioned as being especially preferred are the compounds described in WO 97/31001, in particular 8-cyano-1-cyclopropyl-7-((1S,6S)-2,8-diazabicyclo[4.3.0]nonan-8-yl)-6-fluoro-1,4-dihydro-4-oxo-3-quinolinecarboxylic acid (pradofloxacin), of the formula

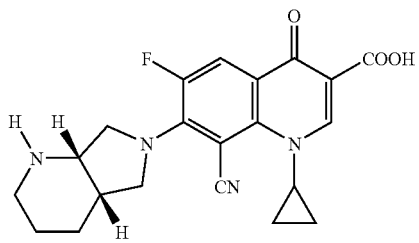

Enrofloxacin is also especially preferably employed:

1-cyclopropyl-7-(4-ethyl-1-piperazinyl)-6-fluoro-1, 4-dihydro-4-oxo-3-quinoline-carboxylic acid

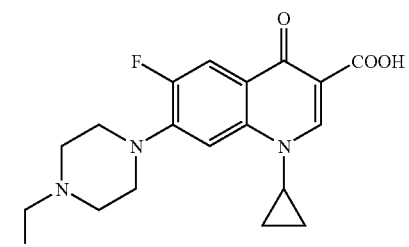

Depsipeptides which may be mentioned are in particular the cyclic depsipeptides. Preferred cyclic depsipeptides are those having 18 to 24 ring atoms, in particular 24 ring atoms.

The depsipeptides having 18 ring atoms include compounds of the general formula (IV):

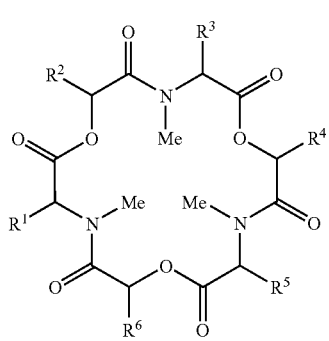

which
R$^1$, R$^3$ and R$^5$ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulfinylalkyl, alkylsulfonylalkyl, carboxyalkyl, alkoxycarbonylalkyl, arylalkoxycarbonyl-alkyl, carbamoylalkyl, aminoalkyl, alkylaminoalkyl, dialkylaminoalkyl, guanidinoalkyl which can optionally be substituted by one or two benzyloxycarbonyl radicals or by one, two, three or four alkyl radicals; alkoxycarbonylaminoalkyl, 9-fluorenylmethoxycarbonyl(Fmoc)aminoalkyl, alkenyl, cycloalkyl, cycloalkylalkyl and optionally substituted arylalkyl, substituents which may be mentioned being halogen, hydroxyl, alkyl and alkoxy, R$^2$, R$^4$ and R$^6$ independently of one another represent hydrogen, straight-chain or branched alkyl having up to 8 carbon atoms, hydroxyalkyl, mercaptoalkyl, alkanoyloxyalkyl, alkoxyalkyl, aryloxyalkyl, alkylthioalkyl, alkylsulfinylalkyl, alkylsulfonylalkyl, carboxyalkyl, alkoxycarbonylalkyl, arylalkoxy-carbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl, optionally substituted aryl or arylalkyl, substituents which may be mentioned being halogen, hydroxyl, alkyl, alkoxy, and their optical isomers and racemates.

Preferred compounds of the formula (IV) are those in which
R$^1$, R$^3$ and R$^5$ independently of one another for straight-chain or branched C$_1$-C$_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxyl-C$_1$-C$_6$-alkyl, in particular hydroxymethyl, 1-hydroxyethyl, C$_1$-C$_4$-alkanoyloxy-C$_1$-C$_6$-alkyl, in particular acetoxymethyl, 1-acetoxyethyl, C$_1$-C$_4$-alkoxy-C$_1$-C$_6$-alkyl, in particular methoxymethyl, 1-methoxyethyl, aryl-C$_1$-C$_4$-alkyloxy-C$_1$-C$_6$-alkyl, in particular benzyloxyethyl, 1-benzyloxyethyl, mercapto-C$_1$-C$_6$-alkyl, in particular mercaptomethyl, C$_1$-C$_4$-alkylthio-C$_1$-C$_6$-alkyl, in particular methylthioethyl, C$_1$-C$_4$-alkylsulfinyl-C$_1$-C$_6$-alkyl, in particular methylsulfinylethyl, C$_1$-C$_4$-alkylsulfonyl-C$_1$-C$_6$-alkyl, in particular methyl-sulfonylethyl, carboxy-C$_1$-C$_6$-alkyl, in particular carboxymethyl, carboxyethyl, C$_1$-C$_4$-alkoxycarbonyl-C$_1$-C$_6$-alkyl, in particular methoxycarbonyl-methyl, ethoxycarbonylethyl, C$_1$-C$_4$-arylalkoxycarbonyl-C$_1$-C$_6$-alkyl, in particular benzyloxycarbonylmethyl, carbamoyl-C$_1$-C$_6$-alkyl, in particular carbamoylmethyl, carbamoylethyl, amino-C$_1$-C$_6$-alkyl, in particular amino-propyl, aminobutyl, C$_1$-C$_4$-alkylamino-C$_1$-C$_6$-alkyl, in particular methyl-aminopropyl, methylaminobutyl, C$_1$-C$_4$-dialkylamino-C$_1$-C$_6$-alkyl, in particular dimethylaminopropyl, dimethylaminobutyl, guanido-C$_1$-C$_6$-alkyl, in particular guanidopropyl, C$_1$-C$_4$-alkoxycarbonylamino-C$_1$-C$_6$-alkyl, in particular tert-butoxycarbonylaminopropyl, tert-butoxycarbonylaminobutyl, 9-fluorenylmethoxycarbonyl(Fmoc)amino-C$_1$-C$_6$-alkyl, in particular 9-fluorenylmethoxycarbonyl(Fmoc)aminopropyl, 9-fluorenylmethoxy-carbonyl(Fmoc)aminobutyl, C$_2$-C$_8$-alkenyl, in particular vinyl, allyl, butenyl, C$_3$-C$_7$-cycloalkyl, in particular cyclopentyl, cyclohexyl, cycloheptyl, C$_3$-C$_7$-cycloalkyl-C$_1$-C$_4$-alkyl, in particular cyclopentylmethyl, cyclohexylmethyl, cycloheptylmethyl, phenyl-C$_1$-C$_4$-alkyl, in particular phenylmethyl which can optionally be substituted by radicals selected from the series consisting of halogen, in particular fluorine, chlorine, bromine or iodine, hydroxyl, C$_1$-C$_4$-alkoxy, in particular methoxy or ethoxy, C$_1$-C$_4$-alkyl, in particular methyl, R$^2$, R$^4$ and R$^6$ independently of one another for straight-chain or branched C$_1$-C$_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxyl-C$_1$-C$_6$-alkyl, in particular hydroxymethyl, 1-hydroxyethyl, C$_1$-C$_4$-alkanoyloxy-C$_1$-C$_6$-alkyl, in particular acetoxymethyl, 1-acetoxyethyl, C$_1$-C$_4$-alkoxy-C$_1$-C$_6$-alkyl, in particular methoxymethyl, 1-methoxyethyl, aryl-C$_1$-C$_4$-alkyloxy-C$_1$-C$_6$-alkyl, in particular benzyloxyethyl, 1-benzyloxyethyl, mercapto-C$_1$-C$_6$-alkyl, in particular mercaptomethyl, C$_1$-C$_4$-alkylthio-C$_1$-C$_6$-alkyl, in particular methylthioethyl, C$_1$-C$_4$-alkylsulfinyl-C$_1$-C$_6$-alkyl, in particular methylsulfinylethyl, C$_1$-C$_4$-alkylsulfonyl-C$_1$-C$_6$-alkyl, in particular methyl-sulfonylethyl, carboxy-C$_1$-C$_6$-alkyl, in particular carboxymethyl, carboxyethyl, C$_1$-C$_4$-alkoxycarbonyl-C$_1$-C$_6$-alkyl, in particular methoxycarbonyl-methyl, ethoxycarbonylethyl, C$_1$-C$_4$-arylalkoxycarbonyl-C$_1$-C$_6$-alkyl, in particular benzyloxycarbonylmethyl, carbamoyl-C$_1$-C$_6$-alkyl, in particular carbamoylmethyl, carbamoylethyl, amino-C$_1$-C$_6$-alkyl, in particular amino-propyl, aminobutyl, C$_1$-C$_4$-alkylamino-C$_1$-C$_6$-alkyl, in particular methyl-aminopropyl, methylaminobutyl, C$_1$-C$_4$-dialkylamino-C$_1$-C$_6$-alkyl, in particular dimethylaminopropyl, dimethylaminobutyl, C$_2$-C$_8$-alkenyl, in particular vinyl, allyl, butenyl, C$_3$-C$_7$-cycloalkyl, in particular cyclopentyl, cyclohexyl, cycloheptyl, C$_3$-C$_7$-cycloalkyl-C$_1$-C$_4$-alkyl, in particular cyclo-pentylmethyl, cyclohexylmethyl, cycloheptylmethyl, phenyl, phenyl-C$_1$-C$_4$-alkyl, in particular phenylmethyl which can optionally be substituted by radicals from the series consisting of halogen, in particular fluorine, chlorine, bromine or iodine, hydroxyl, C$_1$-C$_4$-alkoxy, in particular methoxy or ethoxy, C$_1$-C$_4$-alkyl, in particular methyl, and their optical isomers and racemates.

Especially preferred compounds of the formula (IV) are those in which
R$^1$, R$^3$ and R$^5$ independently of one another for straight-chain or branched C$_1$-C$_8$-alkyl, in particular methyl, ethyl, propyl, isopropyl, butyl, isobutyl, pentyl, isopentyl, sec-pentyl, hexyl, isohexyl, sec-hexyl, heptyl, isoheptyl, sec-heptyl, octyl, isooctyl, sec-octyl, hydroxyl-$C_1$-$C_6$-alkyl, in particular hydroxymethyl, 1-hydroxyethyl, $C_1$-$C_4$-alkanoyloxy-$C_1$-$C_6$-alkyl, in particular acetoxymethyl, 1-acetoxyethyl, $C_1$-$C_4$-alkoxy-$C_1$-$C_6$-alkyl, in particular methoxymethyl, 1-methoxyethyl, aryl-$C_1$-$C_4$-alkyloxy-$C_1$-$C_6$-alkyl, in particular benzyloxymethyl, 1-benzyloxyethyl, $C_1$-$C_4$-alkoxycarbonylamino-$C_1$-$C_6$-alkyl, in particular tert-butoxycarbonylaminopropyl, tert-butoxycarbonylaminobutyl, $C_2$-$C_8$-alkenyl, in particular vinyl, allyl, $C_3$-$C_7$-cycloalkyl, in particular cyclopentyl, cyclohexyl, cycloheptyl, $C_3$-$C_7$-cyclo-alkyl-$C_1$-$C_4$-alkyl, in particular cyclopentylmethyl, cyclohexylmethyl, cycloheptylmethyl, phenyl-$C_1$-$C_4$-alkyl, in particular phenylmethyl which can optionally be substituted by one or more identical or different of the abovementioned radicals, $R^2$, $R^4$ and $R^6$ independently of one another for straight-chain or branched $C_1$-$C_8$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxyl-$C_1$-$C_6$-alkyl, in particular hydroxymethyl, aryl-$C_1$-$C_4$-alkyloxy-$C_1$-$C_6$-alkyl, in particular benzyloxymethyl, 1-benzyloxyethyl, carboxy-$C_1$-$C_6$-alkyl, in particular carboxymethyl, carboxyethyl, $C_1$-$C_4$-alkoxycarbonyl-$C_1$-$C_6$-alkyl, in particular methoxycarbonylmethyl, ethoxycarbonylethyl, $C_1$-$C_4$-aryl-alkoxycarbonyl-$C_1$-$C_6$-alkyl, in particular benzyloxycarbonylmethyl, $C_1$-$C_4$-alkylamino-$C_1$-$C_6$-alkyl, in particular methylaminopropyl, methylaminobutyl, $C_1$-$C_4$-dialkylamino-$C_1$-$C_6$-alkyl, in particular dimethylaminopropyl, dimethylaminobutyl, $C_2$-$C_8$-alkenyl, in particular vinyl, allyl, butenyl, $C_3$-$C_7$-cycloalkyl, in particular cyclopentyl, cyclohexyl, cycloheptyl, $C_3$-$C_7$-cycloalkyl-$C_1$-$C_4$-alkyl, in particular cyclopentylmethyl, cyclohexylmethyl, cycloheptylmethyl, phenyl, phenyl-$C_1$-$C_4$-alkyl, in particular phenylmethyl which can optionally be substituted by one or more identical or different of the abovementioned radicals, and their optical isomers and racemates.

Very especially preferred compounds of the formula (IV) are those in which $R^1$, $R^3$ and $R^5$ independently of one another for straight-chain or branched $C_1$-$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2$-$C_8$-alkenyl, in particular allyl, $C_3$-$C_7$-cycloalkyl-$C_1$-$C_4$-alkyl, in particular cyclohexylmethyl, phenyl-$C_1$-$C_4$-alkyl, in particular phenylmethyl, $R^2$, $R^4$ and $R^6$ independently of one another for straight-chain or branched $C_1$-$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2$-$C_8$-alkenyl, in particular vinyl, allyl, $C_3$-$C_7$-cycloalkyl-$C_1$-$C_4$-alkyl, in particular cyclohexylmethyl, phenyl-$C_1$-$C_4$-alkyl, in particular phenylmethyl which can optionally be substituted by one or more identical or different of the abovementioned radicals, and their optical isomers and racemates.

Compounds of the general formula (IV) which can be used for the purposes of the present invention are all those which can exist in optically active stereoisomeric forms or as racemic mixtures. However, it is preferred to use the optically active stereoisomeric forms of the compounds of the general formula (IV) in accordance with the invention.

The following compounds of the general formula (IV) in which the radicals $R^1$ to $R^6$ have the following meanings may be mentioned specifically:

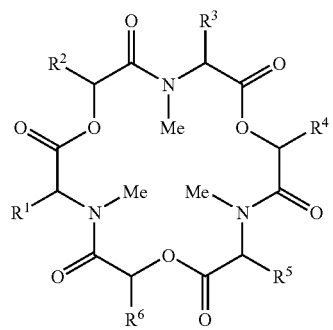

(IV)

| $R^1$ | $R^2$ | $R^3$ | $R^4$ | $R^5$ | $R^6$ |
|---|---|---|---|---|---|
| —CHMeCH$_2$Me | -cyclohexyl | —CHMeCH$_2$Me | —Me | —CHMeCH$_2$Me | —Me |
| —CHMeCH$_2$Me | -cyclohexyl | —CHMeCH$_2$Me | —Me | —CHMeCH$_2$Me | -cyclohexyl |
| —CHMeCH$_2$Me | —CH$_2$—Phe | —CHMeCH$_2$Me | —Me | —CHMeCH$_2$Me | —Me |
| —CHMeCH$_2$Me | —CH$_2$—Phe | —CHMeCH$_2$Me | —Me | —CHMeCH$_2$Me | —CH$_2$—Phe |
| —CHMeCH$_2$Me | —(CH$_2$)$_3$—Me | —CHMeCH$_2$Me | —Me | —CHMeCH$_2$Me | —Me |
| —CHMeCH$_2$Me | —(CH$_2$)$_3$—Me | —CHMeCH$_2$Me | —Me | —CHMeCH$_2$Me | —(CH$_2$)$_3$—Me |
| —CHMe$_2$ | —CH$_2$—Phe | —CHMeCH$_2$Me | —Me | —CHMeCH$_2$Me | —Me |
| —CH$_2$—Phe | —CHMe$_2$ | —CH$_2$—Phe | —CHMe$_2$ | —CHMeCH$_2$Me | —CHMe$_2$ |
| —CH$_2$CHMe$_2$ | —CH$_2$—Phe | —CH$_2$CHMe$_2$ | —Me | —CH$_2$CHMe$_2$ | —CH$_2$—Phe |
| —(CH$_2$)$_3$—Me | —Me | —CHMeCH$_2$Me | —Me | —CHMeCH$_2$Me | —Me |
| —CHMe$_2$ | —Me | —CHMe$_2$ | —Me | —CHMe$_2$ | —Me |
| —CH$_2$—Me | —Me | —CH$_2$—Me | —Me | —CH$_2$—Me | —Me |
| —(CH$_2$)$_2$—Me | —Me | —(CH$_2$)$_2$—Me | —Me | —(CH$_2$)$_2$—Me | —Me |
| —(CH$_2$)$_3$—Me | —Me | —(CH$_2$)$_3$—Me | —Me | —(CH$_2$)$_3$—Me | —Me |

-continued

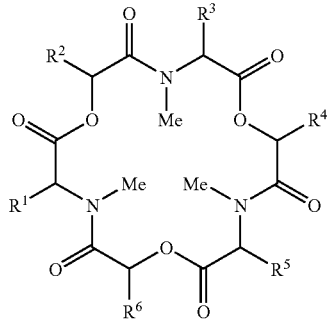

(IV)

| R¹ | R² | R³ | R⁴ | R⁵ | R⁶ |
|---|---|---|---|---|---|
| —CH₂—CH=CH₂ | —Me | —CH₂—CH=CH₂ | —Me | —(CH₂)—CH=CH₂ | —Me |
| —CHMeCH₂Me | —Me | —CHMeCH₂Me | —Me | —CHMeCH₂Me | —CH₂—Me |
| —CHMeCH₂Me | —Me | —CHMeCH₂Me | —Me | —CHMeCH₂Me | —(CH₂)₂—Me |
| —CHMeCH₂Me | —Me | —CHMeCH₂Me | —Me | —CHMeCH₂Me | —(CH₂)₃—Me |
| —CHMeCH₂Me | —Me | —CHMeCH₂Me | —Me | —CH₂Me | —Me |
| —CHMeCH₂Me | —Me | —CHMeCH₂Me | —Me | —(CH₂)₂—Me | —Me |
| -cyclohexyl | —Me | -cyclohexyl | —Me | -cyclohexyl | —Me |
| —CH₂CHMe₂ | -cyclohexyl | -cH₂CHMe₂ | —Me | —CH₂CHMe₂ | -cyclohexyl |
| —CH₂CHMe₂ | -cyclohexyl | -cH₂CHMe₂ | —Me | -cH₂CHMe₂ | —Me |
| —CHMeCH₂Me | —CHMe₂ | —CHMeCH₂Me | —CHMe₂ | —CHMeCH₂Me | —Me |
| —CH₂—Phe | —Me | —CH₂—Phe | —Me | —CH₂—Phe | —Me |
| -cyclohexyl | —Me | -cyclohexyl | —Me | -cyclohexyl | —Me |
| —CHMe₂ | —CHMe₂ | —CHMe | —Me | —CHMe₂ | —Me |
| —CHMe₂ | —CHMe₂ | —CHMe₂ | —CHMe₂ | —CHMe₂ | —Me |
| —CH₂—Me | —CHMe₂ | —CH₂Me | —Me | —CH₂—Me | —Me |
| —CH₂—Me | —CHMe₂ | —CHMe₂ | —CHMe₂ | —CH₂—Me | —Me |
| —(CH₂)₂—Me | —CHMe₂ | —(CH₂)₂—Me | —Me | —(CH₂)₂—Me | —Me |
| —(CH₂)₂—Me | —CHMe₂ | —(CH₂)₂—Me | —CHMe₂ | —(CH₂)₂—Me | —Me |
| —(CH₂)₃—Me | —CHMe₂ | —(CH₂)₃—Me | —Me | —(CH₂)₃—Me | —Me |
| —(CH₂)₃—Me | —CHMe₂ | —(CH₂)₃—Me | —CHMe₂ | —(CH₂)₃—Me | —Me |
| —CH₂—CH=CH₂ | —CHMe₂ | —CH₂—CH=CH₂ | —Me | —CH₂—CH=CH₂ | —Me |
| —CH₂—CH=CH₂ | —CHMe₂ | —CH₂—CH=CH₂ | —CHMe₂ | —CH₂—CH=CH₂ | —Me |
| —Me | —Me | —CHMeCH₂Me | —Me | —CH₂—Me | —Me |
| —Me | —Me | —CHMeCH₂Me | —Me | —(CH₂)₃—Me | —Me |

Me = methyl; Phe = phenyl

A further depsipeptide which may be mentioned is the compound PF 1022 of the following formula, which is disclosed in EP-A 382 173:

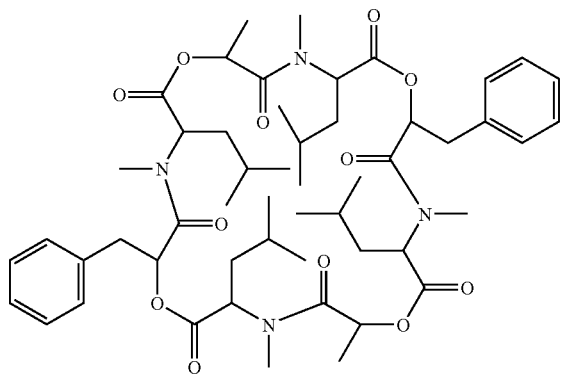

Moreover, depsipeptides which may be mentioned are the compounds disclosed in the PCT application WO 93/19053.

Compounds from the PCT application WO 93/19053 which may be mentioned in particular are the compounds of the following formula:

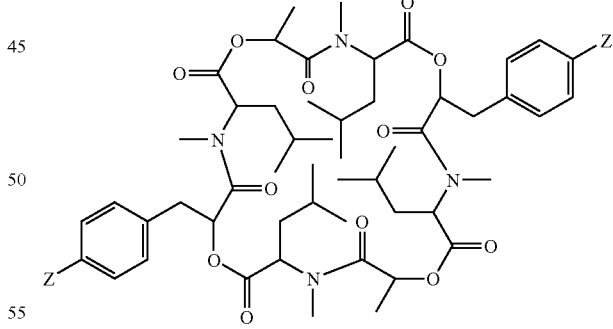

in which

Z represents N-morpholinyl, amino, mono- or dimethylamino.

Especially preferred amongst these is emodepsid, the compound of the above formula in which both radicals Z represent the N-morpholinyl radical.

Compounds which may furthermore be mentioned are those of the following formula:

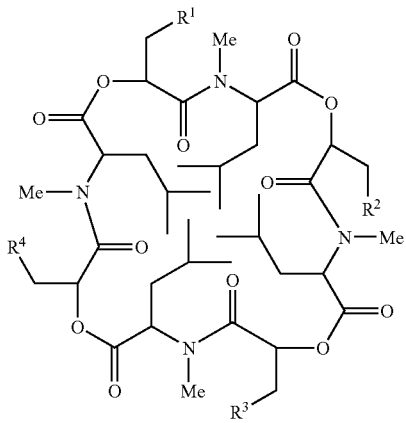

in which

R$^1$, R$^2$, R$^3$, R$^4$ independently of one another represent hydrogen, C$_1$-C$_{10}$-alkyl or aryl, in particular phenyl, which are optionally substituted by hydroxyl, C$_1$-C$_{10}$-alkoxy or halogen.

The compounds of the general formula (IV) are known and can be obtained by the methods described in EP-A-382 173, DE-A 4 317 432, DE-A 4 317 457, DE-A 4 317 458, EP-A-634 408, EP-A-718 293, EP-A-872 481, EP-A-685 469, EP-A-626 375, EP-A-664 297, EP-A-669 343, EP-A-787 141, EP-A-865 498, EP-A-903 347.

The cyclic depsipeptides having 24 ring atoms also include compounds of the general formula (IVa)

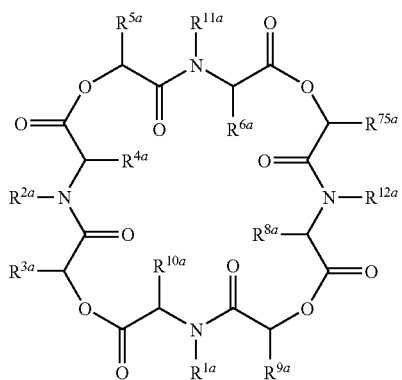

(IVa)

in which

R$^{1a}$, R$^{2a}$, R$^{11a}$ and R$^{12a}$ independently of one another represent C$_{1-8}$-alkyl, C$_{1-8}$-haloalkyl, C$_{3-6}$-cycloalkyl, aralkyl, aryl, R$^{3a}$, R$^{5a}$, R$^{7a}$, R$^{9a}$ independently of one another represent hydrogen or straight-chain or branched C$_{1-8}$-alkyl which can optionally be substituted by hydroxyl, C$_{1-4}$-alkoxy, carboxyl,

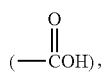

carboxamide,

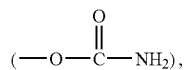

imidazolyl, indolyl, guanidine, —SH or C$_{1-4}$-alkylthio and furthermore represents aryl or aralkyl, both of which can be substituted by halogen, hydroxyl, C$_{1-4}$-alkyl, C$_{1-4}$-alkoxy, R$^{4a}$, R$^{6a}$, R$^{8a}$, R$^{10a}$ independently of one another represent hydrogen, straight-chain C$_{1-5}$-alkyl, C$_{2-6}$-alkenyl, C$_{3-7}$-cycloalkyl, all of which can optionally be substituted by hydroxyl, C$_{1-4}$-alkoxy, carboxy, carboxamide, imidazolyl, indolyl, guanidine, SH or C$_{1-4}$-alkylthio, and represent aryl or aralkyl, both of which can be substituted by halogen, hydroxyl, C$_{1-4}$-alkyl, C$_{1-4}$-alkoxy, and their optical isomers and racemates.

Compounds of the formula (IVa) which are preferably employed are those in which

R$^{1a}$, R$^{2a}$, R$^{11a}$ and R$^{12a}$ independently of one another represent methyl, ethyl, propyl, isopropyl, n-, s-, t-butyl or phenyl, which is optionally substituted by halogen, C$_{1-4}$-alkyl, OH, C$_{1-4}$-alkoxy, and represent benzyl or phenylethyl, both of which can optionally be substituted by the radicals stated for phenyl;

R$^{3a}$ to R$^{10a}$ have the abovementioned meanings.

Especially preferred are compounds of the formula (Ia) in which

R$^{1a}$, R$^{2a}$, R$^{11a}$ and R$^{12a}$ independently of one another represent methyl, ethyl, propyl, isopropyl or n-, s-, t-butyl, R$^{3a}$, R$^{5a}$, R$^{7a}$, R$^{9a}$ represent hydrogen, straight-chain or branched C$_{1-8}$-alkyl, in particular methyl, ethyl, propyl, i-propyl, n-, s-, t-butyl, all of which can optionally be substituted by C$_{1-4}$-alkoxy, in particular methoxy, ethoxy, imidazolyl, indolyl or C$_{1-4}$-alkylthio, in particular methylthio, ethylthio, furthermore represent phenyl, benzyl or phenethyl, all of which can optionally be substituted by halogen, in particular chlorine.

R$^{4a}$, R$^{6a}$, R$^{8a}$, R$^{10a}$ independently of one another represent hydrogen, methyl, ethyl, n-propyl, n-butyl, vinyl, cyclohexyl, all of which can optionally be substituted by methoxy, ethoxy, imidazolyl, indolyl, methylthio, ethylthio, and represent isopropyl, s-butyl and furthermore optionally halogen-substituted phenyl, benzyl or phenylethyl.

The compounds of the formula (IVa) can likewise be obtained by the methods described in EP-A-382 173, DE-A 4 317 432, DE-A 4 317 457, DE-A 4 317 458, EP-A-634 408, EP-A-718 293, EP-A-872 481, EP-A-685 469, EP-A-626 375, EP-A-664 297, EP-A-669 343, EP-A-787 141, EP-A-865 498, EP-A-903 347.

Macrocyclic lactones which may be mentioned are avermectins, 22,23-dihydroavermectins B$_1$ (ivermectins) and milbemycins.

Avermectins and their derivatives which may be mentioned are substances and substance mixtures of macrolid lactones of the general formula (V)

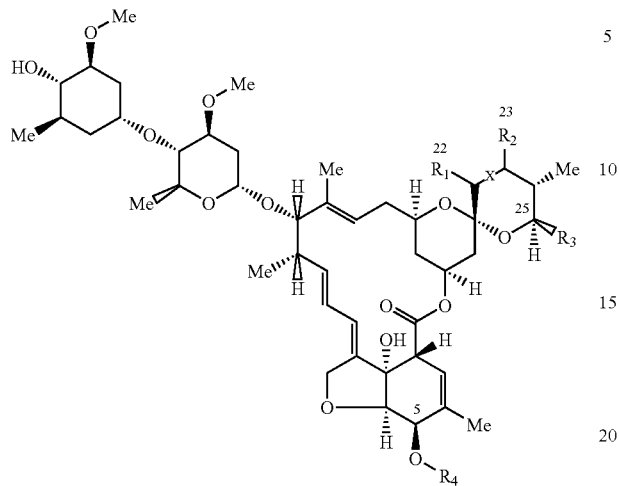

(V)

in which the radicals $R^1$ to $R^4$ have the meanings given in Table 1 which follows and X can represent a single or double bond between the $C_{22}$ and $C_{23}$ position ($—C_{22}R^1—X—C_{23}R^2—$).

In the case of a double bond, no substituents ($R^1$, $R^2$) are present at the $C_{22}$ and $C_{23}$ positions.

TABLE 1

| Macrocyclic lactone | $—C_{22}R^1—X—C_{23}R^2—$ | $R^3$ | $R^4$ |
|---|---|---|---|
| Avermectin $A_{1a}$ | —CH=CH— | -sec-Bu | -Me |
| Avermectin $A_{1b}$ | —CH=CH— | -iso-Pr | -Me |
| Avermectin $A_{2a}$ | —CH$_2$—CHOH— | -sec-Bu | -Me |
| Avermectin $A_{2b}$ | —CH$_2$—CHOH— | -iso-Pr | -Me |
| Avermectin $B_{1a}$ | —CH=CH— | -sec-Bu | —H |
| Avermectin $B_{1b}$ | —CH=CH— | -iso-Pr | —H |
| Avermectin $B_{2a}$ | —CH$_2$—CHOH— | -sec-Bu | —H |
| Avermectin $B_{2b}$ | —CH$_2$—CHOH— | -iso-Pr | —H |
| 22,23-Dihydroavermectin $B_{1a}$ | —CH$_2$—CH$_2$— | -sec-Bu | —H |
| 22,23-Dihydroavermectin $B_{1b}$ | —CH$_2$—CH$_2$— | -iso-Pr | —H |
| Doramectin | —CH=CH— | -Chx | —H |

22,23-Dihydroavermectin $B_1$ represents Ivermectin $B_1$;
sec-Bu = secondary butyl;
iso-Pr = isopropyl;
Chx = cyclohexyl;
-Me = methyl The avermectins and 22,23-dihydroavermectins $B_1$ (ivermectins) of the general formula (I) are generally employed in the form of mixtures. The product abamectin, which essentially comprises the avermectins $B_1$ and their hydrogenation products, the 22,23-dihydroavermectins $B_1$ (ivermectin), is of particular interest.

The macrocyclic lactone compounds referred to as "b" which have an iso-propyl radical at the $C_{25}$ position need not necessarily be separated from the compounds "a", which have a sec-butyl group at the $C_{25}$ position. In general, the mixture of the two substances, which consists of >80% sec-butyl derivative ($B_{1a}$) and <20% iso-propyl derivative ($B_{1b}$) is isolated and can be used in accordance with the invention. In the case of the stereoisomers, the substituents at the $C_{13}$ and $C_{23}$ positions may additionally be arranged either in the α or in the β positions of the ring system, i.e. above or below the molecular plane.

The milbemycins have the same macrolide ring structure as the avermectins or 22,23-dihydroavermectins $B_1$ (ivermectins), but have no substituents attached to them (i.e. lacking oleandrose disaccharide fragment) at position 13 ($R^5$=hydrogen).

Examples which may be mentioned of milbemycins from the class of the macrocyclic lactones are the compounds of the general formula (VI)

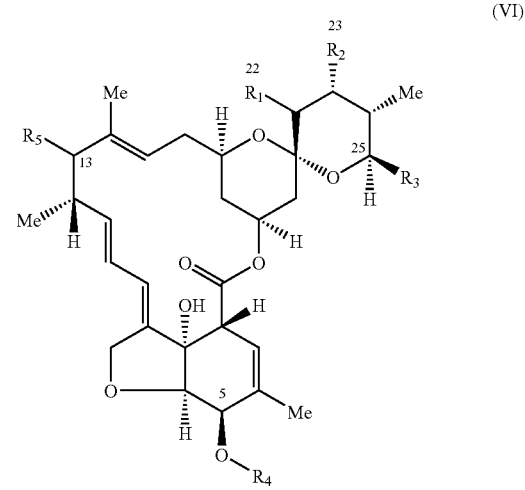

(VI)

in which the radicals $R^1$ to $R^5$ have the meanings given in Table 2 hereinbelow:

TABLE 2

| Macrocyclic lactone | $R^1$ | $R^2$ | $R^3$ | $R^4$ | $R^5$ |
|---|---|---|---|---|---|
| Milbemycin B41 D | —H | —H | -iso-Pr | —H | —H |
| Nemadectin | —H | —OH | ![CH=C(Me)CH(Me)Me] | —H | —H |
| Moxidectin | —H | =N—O—Me | ![CH=C(Me)CH(Me)Me] | —H | —H | iso-Pr = isopropyl

Especially preferred are: avermectin $B_{1a}/B_{1b}$; 22,23-dihydroavermectin $B_{1a}/B_{1b}$ or ivermectin $B_{1a}/B_{1b}$); doramectin; moxidectin.

The compounds of the formula (I) are suitable for use in humans and animals, that is to say in animal keeping and animal breeding in the case of productive livestock, breeding animals, zoo animals, laboratory animals, experimental animals and pets (domestic animals).

Productive livestock and breeding animals include mammals such as, for example, cattle, horses, sheep, pigs, goats, camels, water buffalo, donkeys, rabbits, fallow deer, reindeer; fur bearers such as, for example, mink, chinchilla, racoon; birds such as, for example, chickens, geese, turkeys, ducks, pigeons, ostriches, bird species for domestic and zoo keeping. The possible target groups furthermore include useful and ornamental fish.

Laboratory and experimental animals include mice, rats, gerbils, guinea pigs, golden hamsters, dogs and cats.

Pets include rabbits, hares, reptiles, amphibians and preferably dogs and cats.

The fish include useful, breeding, aquarium and ornamental fish of all ages which live in fresh and salt water. The useful and breeding fish include, for example, carp, (for example koy carp), eel, trout, whitefish, salmon, bream, roach, rudd, chub, sole, plaice, halibut, Japanese yellowtail, (*Seriola quinqueradiata*), Japanese eel (*Anguilla japonica*), red sea bream (*Pagurus major*), sea bass (*Dicentrarchus labrax*), gray mullet (*Mugilus cephalus*), pompano, gilthead sea bream (*Sparus auratus*), *Tilapia* spp., *Cichlid* species such as, for example, Plagioscion, channel catfish etc.

The application can be effected both prophylactically and therapeutically.

The application is effected in the form of suitable preparations, usually via the enteral or parenteral, for example the oral, nasal, intravenous, intraperitoneal, subcutaneous, intramuscular or rectal, route.

Enteral administration is effected for example orally in the form of powders, suppositories, tablets, capsules, pastes, drinks, granules, drenches, bolices, medicated feed or drinking water. Parenteral administration is effected for example in the form of an injection or by implants.

Examples of suitable preparations are:

solutions such as solutions for injection, solutions for nasal administration, if appropriate as a spray, oral solutions, concentrates for oral administration after dilution, gels;

emulsions and suspension for oral administration and for injection; semi-solid preparations;

formulations in which the active substance is incorporated in an ointment base or in oil-in-water or water-in-oil emulsion bases;

solid preparations such as powders, premixes or concentrates, granules, pellets, tablets, bolices, capsules, suppositories; aerosols and inhalants, shaped articles comprising active substance.

Solutions for injection are administered intravenously, intramuscularly, intraperitoneally or subcutaneously.

Solutions for injection are prepared by adding, if appropriate, additives such as solubilizers, acids, bases, buffer salts, antioxidants and preservatives and the active ingredient, or active ingredients, in a suitable solvent or solvent mixture. The solutions are filter-sterilized and packaged.

Solvents which may be mentioned are: physiologically acceptable solvents such as water, alcohols such as ethanol, butanol, benzyl alcohol, glycerol, hydrocarbons, propylene glycol, polyethylene glycols, n-methylpyrrolidone, glycerin formal, Solketal, 2-pyrrolidone, dimethylacetamide, Glycofurol (tetraglycol), benzyl benzoate and mixtures of these.

If appropriate, the active substances can also be dissolved in physiologically acceptable vegetable or synthetic oils which are suitable for injection.

Solubilizers which may be mentioned are: substances which promote the dissolution of the active substance in the main solvent or which prevent the precipitation of the former. Examples are polyvinylpyrrolidone, polyoxyethylated castor oil, polyoxyethylated sorbitan esters and poloxamers.

Preservatives are: benzyl alcohol, ethanol, n-butanol, m-cresol, trichlorobutanol, butylhydroxyanisole (BHA), butylhydroxytoluene (BHT), benzalkonium chloride.

Oral solutions are administered directly. Concentrates are administered orally after previously having been diluted to the use concentration. Oral solutions and concentrates are prepared as described above for the solutions for injection, but sterile procedures can be dispensed with.

The following preservatives are suitable for oral solutions: p-hydroxybenzoic esters, butylhydroxyanisole (BHA), butylhydroxytoluene (BHT) and salts of sorbic acid, propionic acid, lactic acid and benzoic acid.

During the preparation it may be advantageous to add thickeners. Thickeners are; inorganic thickeners such as bentonites, colloidal silica, aluminum monostearate, organic thickeners such as cellulose derivatives, polyvinyl alcohols and their copolymers, acrylates and methacrylates and xanthan.

Emulsions can be administered orally or parenterally.

Emulsions are either of the water-in-oil type or of the oil-in-water type.

They are prepared by dispersing the active substance either in the hydrophobic or in the hydrophilic phase and homogenizing this phase with the solvent of the other phase using suitable emulsifiers and, if appropriate, further adjuvants such as colorants, resorption accelerators, preservatives, antioxidants, UV absorbers, viscosity-increasing substances.

The following may be mentioned as the hydrophobic phase (oils): liquid paraffins, silicone oils, natural vegetable oils such as sesame seed oil, almond oil, peanut oil, soya oil, castor oil, cottonseed oil, synthetic triglycerides such as caprylic/capric triglyceride, triglyceride mixture with vegetable fatty acids of chain length $C_{8-12}$ or with other specifically selected natural fatty acids, partial glyceride mixtures saturated or unsaturated, optionally also hydroxyl-comprising fatty acids, mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$-$C_{18}$, isopropyl myristate, isopropyl palmitate, caprylic/capric esters of saturated fatty alcohols of chain length $C_{12}$-$C_{18}$, isopropyl stearate, oleyl oleate, decyl oleate, ethyl oleate, ethyl lactate, waxy fatty acid esters such as dibutyl phthalate, diisopropyl adipate, ester mixtures related to the latter and other fatty alcohols such as isotridecyl alcohol, 2-octyldodecanol, cetylstearyl alcohol, oleyl alcohol.

Fatty acids such as, for example, oleic acid and their mixtures.

The following may be mentioned as the hydrophilic phase:

water, alcohols such as, for example, propylene glycol, glycerol, sorbitol and their mixtures.

The following may be mentioned as emulsifiers:

non-ionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as disodium N-lauryl-β-iminodipropionate or lecithin;

anionic surfactants such as sodium lauryl sulphate, fatty alcohol ether sulfates, mono/dialkyl polyglycol ether orthophosphoric ester monoethanolamine salt;

cationic surfactants such as cetyltrimethylammonium chloride.

The following may be mentioned as further adjuvants:

substances which increase the viscosity and stabilize the emulsion, such as carboxymethylcellulose, methylcellulose and other cellulose and starch derivatives, polyacrylates, poloxamers, alginates, gelatine, gum arabic, polyvinylpyrrolidone, polyvinyl alcohol, copolymers of methyl vinyl ether and maleic anhydride, polyethylene glycols, waxes, colloidal silica or mixtures of the abovementioned substances.

Suspensions can be administered orally or in the form of an injection. They are prepared by suspending the active substance in an excipient fluid, if appropriate with addition of further adjuvants such as wetters, colorants, resorption accelerators, preservatives, antioxidants, UV absorbers.

Excipient fluids which may be mentioned are all homogeneous solvents and solvent mixtures.

Wetting agents (dispersing agents) which may be mentioned are the surfactants detailed further above.

Further adjuvants which may be mentioned are those detailed further above.

Semisolid preparations can be administered orally. They only differ from the above-described suspensions and emulsions by their higher viscosity.

To prepare solid preparations, the active substance is mixed with suitable excipients, if appropriate with addition of adjuvants, and formulated as desired.

Excipients which may be mentioned are all physiologically acceptable solid inert substances. Inorganic and organic substances may be used for this purpose. Examples of inorganic substances are common salt, carbonates such as calcium carbonate, hydrogen carbonates, aluminum oxides, silicas, clays, precipitated or colloidal silicon dioxide, phosphates.

Examples of organic substances are sugars, cellulose, foodstuffs and feedstuffs such as dry milk, animal meals, fine and coarse cereal meals, starches.

Adjuvants are preservatives, antioxidants, colorants. Antioxidants are sulfites or metabisulfites such as potassium metabisulfite, ascorbic acid, butylhydroxytoluene, butylhydroxyanisole, tocopherol, cysteamine, gallic acid salts such as, for example, propyl gallate, or amino acids such as, for example, cysteine.

Other suitable adjuvants are lubricants and glidants such as, for example, magnesium stearate, stearic acid, talc, bentonites, disintegrants such as starch or crosslinked polyvinylpyrrolidone, binders such as, for example, starch, gelatin or linear polyvinylpyrrolidone, and dry binders such as microcrystalline cellulose.

The compounds of the formula (I) are administered as combination product together with one or more pharmaceutical active substances, it being possible to administer the compound of the formula (I) and active substance simultaneously, separately or staggered over time. In the case of simultaneous administration, active substance(s) and compound of the formula (I) may exist in a joint pharmaceutical formulation.

Ready-to-use preparations comprise the compounds of the formula (I) in concentrations of from 10 ppm to 20% by weight, preferably from 0.01 to 10% by weight.

Preparations which are diluted prior to use comprise the compounds of the formula (I) in concentrations of from 0.5 to 90% by weight, preferably from 1 to 50% by weight.

FORMULATION EXAMPLES

The substances are mixed; if appropriate, filter-sterilized; transferred into suitable containers; if appropriate, autoclaved; and sealed.

Example 1

| Solution | | |
|---|---|---|
| 0.75 g | mebendazole | |
| 3.75 g | compounds of the formulae (A) and (B) in the ratio 9:1 | |
| to 100 g | N-methylpyrrolidone | |

Example 2

| Suspension | | |
|---|---|---|
| 1.0 g | mebendazole | |
| 5.0 g | compounds of the formulae (A) and (B) in the ratio 9:1 | |
| 50 g | N-methylpyrrolidone | |
| to 100 g | Sesame seed oil | |

Example 3

| Suspension | | |
|---|---|---|
| 1.0 g | mebendazole | |
| 5.0 g | compounds of the formulae (A) and (B) in the ratio 9:1 | |
| 70 g | glycerin formal | |
| ad 100 g | Demineralised water | |

Example 4

| Suspension | | |
|---|---|---|
| 1.0 g | mebendazole | |
| 1.0 g | Tween 80 | |
| 5.0 g | compounds of the formulae (A) and (B) in the ratio 9:1 | |
| ad 100 g | Miglyol 812 | |

Example 5

0.72 g   mebendazole
1.13 g   compounds of the formulae (A) and (B) in the ratio 9:1
are made up to 108 ml with an aqueous solution comprising 10% by volume of ethanol.

Example 6

0.72 g   mebendazole
1.13 g   compounds of the formulae (A) and (B) in the ratio 9:1
are made up to 108 ml with an aqueous solution comprising 10% by volume of ethanol and 20% by volume of Cremophor EL.

Biological Examples

Table 3 shows the results of the detection of worm stages in Wistar rats which have been infected experimentally with Angiostrongylus cantonensis, following oral treatment with an aqueous mebendazole suspension (10 mg/kg body weight) and mebendazole (0.33 mg/kg body weight) in different carrier systems in % in comparison with the infection controls and carrier control.

TABLE 3

| Type of experiment | Worm detection in the brain |
| --- | --- |
| Infection control | 55 worms detected, corresponds to 100% |
| Mebendazole aqueous suspension, 10 mg/kg body weight | 98.2% |
| Enhancer* alone | 100% |
| Enhancer* + Cremaphor | 100% |
| Mebendazole (0.33 mg/kg body weight) + enhancer* (solution as described in Ex. 1) | 4% |
| Mebendazole (0.33 mg/kg body weight) + enhancer* (solution as described in Example 6) | 6% |

*enhancer: compounds of the formulae (A) and (B) in the ratio 9:1

Each rat was infected with precisely 60 L3 larvae. From day 5 post-infection onwards, mebendazole was administered once daily on three successive days at the dosage rates and in the formulations stated. The worms were detected on day 21 post-infection.

The medicament mebendazole is translocated across the blood-brain barrier with the aid of the carrier system. This results in significant worm reduction in the brain at a more than 30-fold reduced mebendazole dose.

We claim:

1. A method to improve permeation of a pharmaceutically active substance across a cell barrier comprising co-administering the pharmaceutically active substance with compound 1:

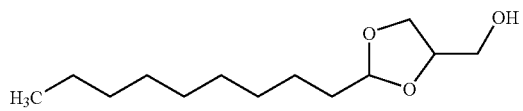

and compound 2:

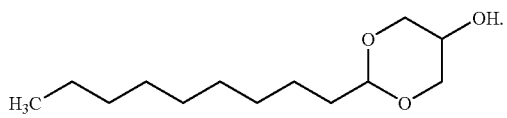

2. The method of claim 1, wherein compound 1 and compound 2 are present in a ratio of about 9:1.

3. The method of claim 1, wherein the pharmaceutically active substance is an antibiotic or antiparasitic compound.

4. The method of claim 3, wherein the pharmaceutically active substance is a fluoroquinolone.

5. The method of claim 3, wherein the pharmaceutically active substance is mebendazole.

6. A composition to improve permeation of a pharmaceutically active substance across a cell barrier comprising compound 1:

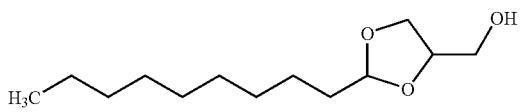

and compound 2:

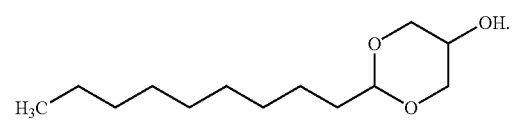

and a pharmaceutically acceptable carrier.

7. The composition of claim 6, wherein compound 1 and compound 2 are present in a ratio of about 9:1.

8. The method of claim 1, wherein the administration is enteral or parenteral.

9. The method of claim 8, wherein the administration is an enteral administration selected from the group consisting of oral, nasal, or rectal.

10. The method of claim 8, wherein the administration is a parenteral administration selected from the group consisting of intravenous, intraperitoneal, subcutaneous, and intramuscular.

11. A method to improve permeation of a pharmaceutically active substance across the blood-brain barrier comprising co-administering the pharmaceutically active substance with compound 1:

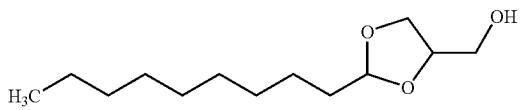

and compound 2:

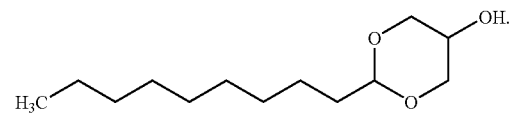

* * * * *